United States Patent
Kaneko et al.

(10) Patent No.: US 12,116,471 B2
(45) Date of Patent: Oct. 15, 2024

(54) CHLOROPRENE COPOLYMER LATEX AND PRODUCTION METHOD THEREFOR

(71) Applicant: SHOWA DENKO K.K., Tokyo (JP)

(72) Inventors: Shu Kaneko, Tokyo (JP); Masahiro Ogawa, Tokyo (JP); Akira Shibuya, Tokyo (JP)

(73) Assignee: Resonac Corporation, Tokyo (JP)

( * ) Notice: Subject to any disclaimer, the term of this patent is extended or adjusted under 35 U.S.C. 154(b) by 389 days.

(21) Appl. No.: 17/615,214

(22) PCT Filed: Oct. 23, 2020

(86) PCT No.: PCT/JP2020/039882
§ 371 (c)(1),
(2) Date: Nov. 30, 2021

(87) PCT Pub. No.: WO2021/079981
PCT Pub. Date: Apr. 29, 2021

(65) Prior Publication Data
US 2022/0227976 A1     Jul. 21, 2022

(30) Foreign Application Priority Data

Oct. 25, 2019   (JP) ................... 2019-194507

(51) Int. Cl.
| | | |
|---|---|---|
| C08L 11/02 | (2006.01) | |
| A41D 19/00 | (2006.01) | |
| A41D 19/04 | (2006.01) | |
| A61B 42/10 | (2016.01) | |
| B29C 41/00 | (2006.01) | |
| B29C 41/14 | (2006.01) | |
| C08J 5/02 | (2006.01) | |
| B29K 105/00 | (2006.01) | |
| B29L 31/48 | (2006.01) | |

(52) U.S. Cl.
CPC .......... *C08L 11/02* (2013.01); *A41D 19/0055* (2013.01); *A41D 19/04* (2013.01); *A61B 42/10* (2016.02); *B29C 41/003* (2013.01); *B29C 41/14* (2013.01); *C08J 5/02* (2013.01); *B29K 2011/00* (2013.01); *B29K 2105/0064* (2013.01); *B29L 2031/4864* (2013.01); *C08J 2311/02* (2013.01); *C08J 2493/04* (2013.01); *C08L 2201/52* (2013.01)

(58) Field of Classification Search
CPC ......... C08L 11/02; C08L 2201/52; C08J 5/02; C08J 2311/02; C08J 2493/04; A61B 42/10; A41D 19/04; A41D 19/0055; B29K 2105/0064; B29C 41/003; B29C 41/14
USPC ........................................... 524/213
See application file for complete search history.

(56) References Cited

FOREIGN PATENT DOCUMENTS

| | | | |
|---|---|---|---|
| JP | 2003-55409 A | | 2/2003 |
| JP | 2007-106994 A | | 4/2007 |
| JP | 2009185136 A | * | 8/2009 |
| JP | 2011122141 A | * | 6/2011 |
| JP | 2019-44116 A | | 3/2019 |
| JP | 2019-143002 A | | 8/2019 |

OTHER PUBLICATIONS

Translation of JP 2009-185136 (patents application 2008-024770), Aug. 20, 2009. (Year: 2009).*
Translation of JP 2011-122141 (patens application 2010-247999), Jun. 23, 2011. (Year: 2011).*
International Search Report issued Dec. 15, 2020 in International Application No. PCT/JP2020/039882.
Written Opinion of the International Searching Authority issued Dec. 15, 2020 in International Application No. PCT/JP2020/039882.

* cited by examiner

*Primary Examiner* — Hui H Chin
(74) *Attorney, Agent, or Firm* — Sughrue Mion, PLLC

(57) ABSTRACT

One embodiment of the present invention relates to a chloroprene copolymer latex, a method for producing a chloroprene copolymer latex, a chloroprene copolymer latex composition, and a molded article or dipped product of a chloroprene copolymer rubber. The chloroprene copolymer latex is a latex of a chloroprene copolymer including monomer units derived from 2-chloro-1,3-butadiene (chloroprene) and monomer units derived from 2-methyl-1,3-butadiene, wherein the tetrahydrofuran insoluble content in the chloroprene copolymer is 20% by mass or less, and the proportion of the monomer units derived from 2-methyl-1,3-butadiene is 10 to 27 mol % in the chloroprene copolymer.

9 Claims, No Drawings

CHLOROPRENE COPOLYMER LATEX AND PRODUCTION METHOD THEREFOR

CROSS REFERENCE TO RELATED APPLICATIONS

This application is a National Stage of International Application No. PCT/JP2020/039882 filed on Oct. 23, 2020, claiming priority based on Japanese Patent Application No. 2019-194507 filed on Oct. 25, 2019.

TECHNICAL FIELD

The present invention relates to a latex including, as a main component, a copolymer of 2-chloro-1,3-butadiene (chloroprene) and 2-methyl-1,3-butadiene, a production method therefor, and a molded article, particularly a dip-molded product, using a composition including the latex.

BACKGROUND ART

Isoprene rubber (IR) and chloroprene rubber (CR) are synthetic rubber having flexibility equivalent to that of natural rubber. Thus, isoprene rubber or chloroprene rubber has been recently used, instead of natural rubber, in a material for a product obtained by dip-molding of a composition (dip-molded products), especially surgical glove, as a countermeasure against allergy. Although isoprene rubber has high flexibility and provides an excellent tactile sensation for medical practitioners, the isoprene rubber does not fully meet the needs of the market because of its high cost. On the other hand, chloroprene rubber is less expensive than isoprene rubber but is problematically inferior in touch because of its lower flexibility than that of isoprene rubber. Chloroprene rubber also problematically has low production efficiency because of, for example, requiring vulcanization treatment at a high temperature for a long period in order to achieve intended strength.

The physical properties of synthetic rubber change with time after molding. Specifically, isoprene rubber disadvantageously degrades over time to become soft and chloroprene rubber disadvantageously degrades over time to become hard.

For instance, Patent Literatures 1 and 2 disclose techniques for improving the flexibility of chloroprene rubber, but a vulcanization step at a high temperature for a long period is required therefor. Patent Literature 3 discloses a technique for reducing the temperature and treatment time in the vulcanization step, but a problem with the flexibility arises.

CITATION LIST

Patent Literature

Patent Literature 1: Japanese Patent Laid-Open No. 2007-106994
Patent Literature 2: Japanese Patent Laid-Open No. 2019-143002
Patent Literature 3: Japanese Patent Laid-Open No. 2019-044116

SUMMARY OF INVENTION

Technical Problem

It is an object of the present invention to solve the problems of the conventional arts and to inexpensively provide a chloroprene copolymer latex that can be vulcanized under milder conditions than conventional chloroprene copolymer latex and can provide a molded product having excellent flexibility.

Solution to Problem

The present inventors have intensively studied to solve the above problems and, as a result, have found that the above problems can be solved by, in a latex of a chloroprene copolymer including monomer units derived from chloroprene and monomer units derived from 2-methyl-1,3-butadiene, setting the proportion of the monomer units derived from 2-methyl-1,3-butadiene included in the chloroprene copolymer within a specific range and setting the tetrahydrofuran insoluble content in the chloroprene copolymer to a predetermined value or less, thereby having completed the present invention.

That is, the present invention relates to a chloroprene copolymer latex, a production method therefor, a latex composition thereof, and a rubber composition and a dip-molded product provided by curing the composition, according to the following [1] to [12].

[1] A latex of a chloroprene copolymer comprising monomer units derived from 2-chloro-1,3-butadiene (chloroprene) and monomer units derived from 2-methyl-1,3-butadiene, wherein a tetrahydrofuran insoluble content in the chloroprene copolymer is 20% by mass or less, and a proportion of the monomer units derived from 2-methyl-1,3-butadiene in the chloroprene copolymer is 10 to 27 moil.

[2] The latex according to [1], wherein a tetrahydrofuran soluble component in the chloroprene copolymer has a weight average molecular weight of 400,000 or more.

[3] The latex according to [1] or [2], wherein the chloroprene copolymer further comprises 0.01 to 10 mol % of third monomer units.

[4] The latex according to [3], wherein the third monomer units are monomer units derived from 2,3-dichloro-1,3-butadiene.

[5] A method for producing a chloroprene copolymer latex, comprising a step of emulsion-copolymerizing monomer components containing 2-chloro-1,3-butadiene (chloroprene) and 2-methyl-1,3-butadiene, wherein a proportion of 2-methyl-1,3-butadiene in the total monomer components is 2 to 40 mol %, and a polymerization conversion of the total monomers is 61 to 90% by mass.

[6] The method for producing a chloroprene copolymer latex according to [5], wherein an alkylmercaptan is used as a chain transfer agent.

[7] The method for producing a chloroprene copolymer latex according to [5] or [6], wherein a potassium salt of rosin acid is used as an emulsifier.

[8] A chloroprene copolymer latex composition comprising:
100 parts by mass of solid content of the chloroprene copolymer latex according to any of [1] to [4];
0.1 to 20.0 parts by mass of a metal oxide (B);
0.1 to 10.0 parts by mass of a vulcanization accelerator (C);
0.1 to 10.0 parts by mass of sulfur (D); and
0.1 to 10.0 parts by mass of an antioxidant (E).

[9] A molded article of a chloroprene copolymer rubber, provided by curing the chloroprene copolymer latex composition according to [8].

[10] A dip-molded product provided by molding the chloroprene copolymer latex composition according to [8] by a dipping method followed by curing.

[11] The dip-molded product according to [10], wherein the dip-molded product is gloves.

[12] The dip-molded product according to [11], wherein the dip-molded product is medical disposable gloves.

Advantageous Effect of Invention

The chloroprene copolymer latex composition of the present invention can be vulcanized under mild conditions to provide a molded article (molded article of a chloroprene copolymer rubber) having excellent flexibility. The molded article related to the present invention has stability over time (thermal degradation resistance) and can be suitably used for dip-molded products, particularly medical disposable gloves.

DESCRIPTION OF EMBODIMENT

Hereinafter, embodiments of the present invention will be described in detail, but the present invention is not limited to the configurations of the following embodiments. In the statements herein and also in claims, "to" indicating a numerical range means numerical values between the lower limit and the upper limit of the range, both inclusive.

The chloroprene copolymer latex (A) of the present embodiment is a latex provided by dispersing particulates of a chloroprene copolymer in a solvent such as water. The chloroprene copolymer included in the chloroprene copolymer latex (A) includes at least structures (monomer units) derived from 2-chloro-1,3-butadiene (chloroprene) (A-1) and from 2-methyl-1,3-butadiene (A-2). The monomer units constituting the chloroprene copolymer may be only 2-chloro-1,3-butadiene (A-1) and 2-methyl-1,3-butadiene (A-2).

Specifically, the proportion of 2-methyl-1,3-butadiene (A-2) is 10 to 27 mol %, preferably 10 to 25 mol %, more preferably 11 to 15 mol %, with respect to 100 mol % of the total monomer units constituting the chloroprene copolymer.

If the proportion of the 2-methyl-1,3-butadiene (A-2) monomer units in the chloroprene copolymer is less than 10 mol %, the tensile strength of a molded article provided by vulcanization at 100° C. decreases. Also if the proportion of the 2-methyl-1,3-butadiene (A-2) monomer units in the copolymer is more than 27 mol %, the strength of the molded article decreases. That is, with a proportion of the 2-methyl-1,3-butadiene (A-2) monomer units of 10 to 27 mol %, a molded article after the vulcanization can exhibit favorable strength when the chloroprene copolymer is vulcanized at 100° C.

The chloroprene copolymer can include monomer units derived from the monomer (A-3) as long as the object of the present invention is not impaired, in addition to the structures (monomer units) derived from 2-chloro-1,3-butadiene (A-1) and monomer units derived from 2-methyl-1,3-butadiene (A-2). Here, the monomer (A-3) is a monomer other than 2-chloro-1,3-butadiene (A-1) or 2-methyl-1,3-butadiene (A-2), and is copolymerizable with at least one of 2-chloro-1,3-butadiene (A-1) and 2-methyl-1,3-butadiene (A-2). The monomer (A-3) may be a monomer copolymerizable with both 2-chloro-1,3-butadiene (A-1) and 2-methyl-1,3-butadiene (A-2). Examples of the monomer (A-3) include butadiene, 2,3-dichloro-1,3-butadiene, styrene, acrylonitrile, acrylic acid and esters thereof, and methacrylic acid and esters thereof. The chloroprene copolymer may include, as required, structures derived from two or more monomers, as the structure derived from the monomer (A-3). When the chloroprene copolymer includes the structure derived from the monomer (A-3) units, the proportion (upper limit) of the monomer (A-3) in the total monomer components constituting the chloroprene polymer is preferably 10.0 mol % or less, more preferably 8.0 mol % or less, still more preferably 5.0 mol % or less. When the chloroprene copolymer includes the structure derived from the monomer (A-3), the proportion (lower limit) of the monomer (A-3) in the total monomer components constituting the chloroprene polymer is preferably 0.01 mol % or more, more preferably 0.5 mol % or more, still preferably 1.0 mol % or more. When the proportion of the structure derived from the monomer (A-3) is 10.0 mol % or less, the tensile strength and elongation of the molded article are favorable, and the stability over time of the flexibility of the molded article is favorable.

The amount of the tetrahydrofuran (THF) insoluble component at 25° C. of the chloroprene copolymer of the present embodiment is 20% by mass or less, preferably 10% by mass or less, more preferably 5% by mass or less. The tetrahydrofuran insoluble content is a gelled product of polymer chains via three-dimensional crosslinking in chloroprene copolymer particles. The amount of the tetrahydrofuran insoluble content can be measured by a method employed in examples described below.

When the amount of the tetrahydrofuran insoluble content of the chloroprene copolymer at 25° C. is 20% by mass or less, the flexibility and tensile strength of the molded article are favorable. The amount of the tetrahydrofuran insoluble content of the chloroprene copolymer of the present invention is preferably 0% by mass or more, more preferably 0.1% by mass or more, still more preferably 1.5% by mass or more. The amount of the tetrahydrofuran insoluble content of the chloroprene copolymer can be controlled by adjusting the polymerization conversion and the amount of chain transfer agent in production of the chloroprene copolymer.

For example, an increase in the polymerization conversion tends to increase the amount of the tetrahydrofuran insoluble content in the chloroprene copolymer. The polymerization conversion can be controlled via the polymerization time and polymerization temperature of the chloroprene copolymer. A longer polymerization time tends to lead to a higher polymerization conversion, and a higher polymerization temperature tends to lead to a higher polymerization conversion. On the other hand, an increase in the amount of the chain transfer agent tends to reduce the amount of the tetrahydrofuran insoluble content in the chloroprene copolymer.

The weight average molecular weight of the tetrahydrofuran soluble component at 25° ° C. of the chloroprene copolymer is preferably 400,000 or more, more preferably 500,000 or more, still more preferably 550,000 or more, as measured by the method or conditions employed in examples described later. When the weight average molecular weight of the tetrahydrofuran soluble component at 25° C. of the chloroprene copolymer is 400,000 or more, a molded article having favorable mechanical properties can be provided. The weight average molecular weight of the tetrahydrofuran soluble component at 25° C. of the chloroprene copolymer is preferably 3,000,000 or less, more preferably 2,000,000 or less, still more preferably 900,000 or less. When the weight average molecular weight of the tetrahydrofuran soluble component at 25° C. of the chloroprene copolymer is 3,000,000 or less, a molded article having favorable flexibility and tensile strength can be provided.

[Method for Producing Chloroprene Copolymer Latex (A)]

As a method for producing the chloroprene copolymer latex (A), a method of radically polymerizing monomers in an aqueous emulsion is simple and industrially advantageous.

Emulsion polymerizing 2-chloro-1,3-butadiene (A-1) and 2-methyl-1,3-butadiene (A-2), or 2-chloro-1,3-butadiene (A-1), 2-methyl-1,3-butadiene (A-2), and the monomer (A-3) using an emulsifier can provide a copolymer latex (A) including chloroprene copolymer particles dispersed in water. The polymerization temperature on the emulsion polymerization is preferably 20 to 35° C., and the polymerization time is preferably 5 to 8 hours. The polymerization temperature and polymerization time on the emulsion polymerization are preferably within the above ranges because a desired polymerization conversion is achieved.

The content of 2-methyl-1,3-butadiene in the chloroprene copolymer of the present invention can be adjusted by means of, for example, the proportions of 2-chloro-1,3-butadiene (A-1) and 2-methyl-1,3-butadiene (A-2) fed for polymerization and the polymerization conversion thereof.

A higher proportion of 2-methyl-1,3-butadiene (A-2) fed for polymerization with respect to the total monomers can finally result in a large content of the monomer units derived from 2-methyl-1,3-butadiene (A-2) with respect to the chloroprene copolymer. However, 2-methyl-1,3-butadiene (A-2) has lower reactivity at the beginning of the emulsion polymerization than that of 2-chloro-1,3-butadiene (A-1). Thus, a larger proportion of 2-methyl-1,3-butadiene (A-2) fed tends to retard the progress of the polymerization to lengthen the reaction time.

As the polymerization of the chloroprene copolymer proceeds, 2-methyl-1,3-butadiene (A-2) is more likely to be incorporated in the polymer. Then, an increase in the polymerization conversion on polymerization for the chloroprene copolymer can lead to an increase in the content of the monomer units derived from 2-methyl-1,3-butadiene with respect to the final chloroprene copolymer. With a low polymerization conversion, remaining monomers increase, which requires an effort of removing the remaining monomers, and moreover, mechanical properties of the molded article are degraded.

In view of the above, the content of 2-methyl-1,3-butadiene (A-2) in the total monomer components used is preferably 2 to 40 mol %, more preferably 10 to 30 mol %, still more preferably, 15 to 25 mol %, in view of effectively providing the chloroprene copolymer in the present invention. The polymerization conversion of the total monomers is preferably 61 to 90% by mass, more preferably 75 to 87% by mass, still more preferably 75 to 86% by mass. When the polymerization conversion of the total monomers is 90% by mass or less, the quality of the chloroprene copolymer provided by the polymerization is favorable, and the physical properties of a molded article provided from the chloroprene copolymer latex (A) are also favorable.

The emulsifier for the emulsion polymerization is preferably an anionic surfactant. Examples of the anionic surfactant include rosin acid soap, sodium salts of naphthalenesulfonic acid condensates, sodium salts of dodecylbenzenesulfonic acid, and sodium salts of dodecylsulfuric acid. Usual rosin acid soap can be used in view of simple operation for solidification. Particularly in view of coloring stability, a sodium salt and/or potassium salt of disproportionated rosin acid can be used. In view of the polymerization rate, a potassium salt of disproportionated rosin acid is more preferred.

The amount of the emulsifier used is 0.5 to 20.0 parts by mass, more preferably 1.0 to 10.0 parts by mass, still more preferably 1.5 to 5.0 parts by mass, per 100 parts by mass of the total of all the monomers: 2-chloro-1,3-butadiene (A-1), 2-methyl-1,3-butadiene (A-2), and the monomer (A-3). When the amount of the emulsifier used is 0.5 parts by mass or more, poor emulsification is unlikely to occur, and exotherm due to the polymerization can be controlled. When the amount of the emulsifier used is 0.5 parts by mass or more, problems do not arise, such as generation of aggregates and poor appearance of products. On the other hand, when the amount of the emulsifier used is 20.0 parts by mass or less, the emulsifier such as rosin acid does not remain in the chloroprene copolymer, and adhesion is unlikely to occur in the chloroprene copolymer. Thus, when the amount of the emulsifier used is 20.0 parts by mass or less, problems of processability and handleability due to, for example, adhesion of the chloroprene copolymer latex composition to the mold (former) on molding or adhesion of a molded article on use does not occur, and the color tone of the molded article does not deteriorate.

As a polymerization initiator, a usual radical polymerization initiator can be used. For example, an organic or inorganic peroxide such as benzoyl peroxide, potassium peroxide, ammonium persulfate, cumene hydroperoxide, and t-butyl hydroperoxide, or an azo compound such as azobisisobutyronitrile is used in the case of emulsion polymerization. One of the polymerization initiators may be used singly, or two or more thereof may be used in combination.

In polymerization of the chloroprene copolymer of the present embodiment, a chain transfer agent is preferably used for adjusting the amount of the tetrahydrofuran insoluble content. The amount of the chain transfer agent used is preferably 0.01 to 15.0 parts by mass, more preferably 0.05 to 10.0 parts by mass, still more preferably 0.1 to 1.0 parts by mass, per 100 parts by mass of the total of all the monomers: 2-chloro-1,3-butadiene (A-1), 2-methyl-1,3-butadiene (A-2), and the monomer (A-3).

The chain transfer agent is not particularly limited, and a known chain transfer agent can be used, including an alkylmercaptan such as n-dodecylmercaptan, n-decylmercaptan, octylmercaptan, or tert-dodecylmercaptan, a dialkyl xanthogen disulfide such as diisopropyl xanthogen disulfide or diethyl xanthogen disulfide, or iodoform. More preferred is an alkylmercaptan, and still more preferred is n-dodecylmercaptan.

Setting the polymerization conversion to 61 to 90% by mass and the amount of the chain transfer agent used to 0.01 to 15.0 parts by mass can adjust the amount of the tetrahydrofuran insoluble content in the chloroprene copolymer within a desired range (20% by mass or less).

In polymerization of the chloroprene copolymer, a cocatalyst may be used with the polymerization initiator, if desired. The cocatalyst that can be used with the polymerization initiator is not particularly limited, and a common cocatalyst can be used. Examples of the cocatalyst include anthraquinonesulfonates, potassium sulfite, sodium disulfite, sodium sulfite, tetraethylenepentamine, and N,N-dimethyl-p-toluidine. One of the cocatalysts may be used singly, or two or more thereof may be used in combination.

Generally in emulsion polymerization, a polymerization terminator is added when a predetermined polymerization conversion is reached to thereby stop the polymerization reaction, in order to provide a polymer having a desired molecular weight and a desired molecular weight distribution. A polymerization terminator may be used also in the embodiment of the present invention. The type of polymerization terminator is not particularly limited, and a polymerization terminator usually used can be used, including phenothiazine, para-t-butylcatechol, hydroquinone, hydroquinone monomethylether, and diethylhydroxylamine. One of the polymerization terminators may be used singly, or two or more thereof may be used in combination.

In addition, a stabilizer such as an acid acceptor and/or an antioxidant may be blended to the chloroprene copolymer latex (A) as long as the object of the present invention is not impaired.

[Chloroprene Copolymer Latex Composition]

The chloroprene copolymer latex composition according to one embodiment of the present invention includes the solid content of the chloroprene copolymer latex (A) provided by the above polymerization method, a metal oxide (B), a vulcanization accelerator (C), sulfur (D), and an antioxidant (E). The solid content of the chloroprene copolymer latex (A) here refers to a component provided when allowing the chloroprene copolymer latex (A) to stand in an oven at 141° C. for 30 minutes for drying. The component is provided by removing the solvent such as water, which is the dispersion medium, from the chloroprene copolymer latex (A). The chloroprene copolymer latex composition may contain a solvent such as water in the chloroprene copolymer latex (A).

The chloroprene copolymer latex composition may further include 0.1 to 20.0 parts by mass of the metal oxide (B), 0.1 to 10.0 parts by mass of the vulcanization accelerator (C), 0.1 to 10.0 parts by mass of the sulfur (D), and 0.1 to 10.0 parts by mass of the antioxidant (E), per as 100 parts by mass of the solid content in the chloroprene copolymer latex (A). Vulcanizing the chloroprene copolymer latex composition prepared in this formulation provides a rubber molded article (e.g., a film) having improved stability over time of the flexibility. Among the materials used for blending, a water-insoluble component and a component that destabilizes the colloid state of the chloroprene copolymer latex are each made into an aqueous dispersion in advance, and then the aqueous dispersion is added to the chloroprene copolymer latex.

The type of the metal oxide (B) is not particularly limited. Examples thereof that can be used include zinc oxide, lead oxide, and trilead tetraoxide, and zinc oxide is particularly preferred. One of the metal oxides (B) may be used singly, or two or more thereof may be used in combination.

The amount of the metal oxide (B) contained in the chloroprene copolymer latex composition according to the present embodiment is usually 0.1 to 20.0 parts by mass, preferably 0.5 to 15.0 parts by mass, more preferably 1.0 to 10.0 parts by mass, per 100 parts by mass of the solid content in the chloroprene copolymer latex (A). When the amount of the metal oxide (B) is 0.1 parts by mass or more, a moderate vulcanization rate can be achieved. When the amount of the metal oxide (B) is 20.0 parts by mass or less, a favorable crosslinked structure is provided by the vulcanization treatment, and scorching is unlikely to occur. The colloid state of the chloroprene copolymer latex composition is stabilized, and thus, problems such as precipitation are unlikely to arise.

The type of the vulcanization accelerator (C) is not particularly limited, and it is possible to use a vulcanization accelerator commonly used for vulcanization treatment of an isoprene-based polymer latex or a chloroprene-based polymer latex. Examples thereof include thiuram-based, dithiocarbamate-based, thiourea-based, guanidine-based, and thiazole-based vulcanization accelerators.

Examples of the thiuram-based vulcanization accelerator include tetraethylthiuram disulfide and tetrabutylthiuram disulfide. Examples of the dithiocarbamate-based vulcanization accelerator include sodium dibutyldithiocarbamate, zinc dibutyldithiocarbamate, and zinc diethylthiodicarbamate. Examples of the thiourea-based vulcanization accelerator include ethylene thiourea, diethyl thiourea, trimethyl thiourea, and N,N'-diphenyl thiourea (DPTU). Examples of the guanidine-based vulcanization accelerator include diphenyl guanidine (DPG) and diorthotoluyl guanidine. Examples of the thiazole-based vulcanization accelerator include 2-mercaptobenzothiazole, di-2-benzothiazolyl disulfide, and zinc 2-mercaptobenzothiazole. One of the vulcanization accelerators (C) may be used singly, or two or more thereof may be used in combination.

The amount of the vulcanization accelerator (C) contained in the chloroprene copolymer latex composition according to the present embodiment is usually 0.1 to 10.0 parts by mass, preferably 0.3 to 5.0 parts by mass, more preferably 0.5 to 2.5 parts by mass, per 100 parts by mass of the solid content in the chloroprene copolymer latex (A). When the amount of the vulcanization accelerator (C) is within this range, a moderate vulcanization rate can be achieved, lack of crosslinked structures due to insufficient vulcanization is unlikely to occur, and additionally, scorching is unlikely to occur. Also, when the amount of the vulcanization accelerator (C) is set within the above range, a molded article provided from the chloroprene copolymer latex composition according to the present embodiment has a moderate vulcanization density, and the flexibility of the molded article is thus allowed to fall within an appropriate range.

The type of the sulfur (D) is not particularly limited. Powdered sulfur, precipitated sulfur, colloidal sulfur, surface-treated sulfur, and insoluble sulfur, as well as sulfur-containing compounds such as polysulfides and polymeric polysulfides (except for the above vulcanization accelerators) can be used. One of the sulfurs (D) may be used singly, or two or more thereof may be used in combination. The amount of the sulfur (D) contained in the chloroprene copolymer latex composition according to the present embodiment is usually 0.1 to 10.0 parts by mass, preferably 0.2 to 7.0 parts by mass, more preferably 0.45 to 2.0 parts by mass, per 100 parts by mass of the solid content in the chloroprene copolymer latex (A). When the amount of the sulfur (D) is within this range, a moderate vulcanization rate can be achieved, lack of crosslinked structures due to insufficient vulcanization treatment is unlikely to occur, and additionally, scorching is unlikely to occur. The colloid state of the chloroprene copolymer latex composition is stabilized, and thus, problems such as precipitation are unlikely to occur.

The type of the antioxidant (E) is not particularly limited. When a molded article having high heat resistance is desirable, an antioxidant that prevents thermal aging and an antioxidant that prevents ozone aging are preferably used in combination.

Examples of the antioxidant that prevents thermal aging include diphenylamine-based antioxidants such as octylated diphenylamine, p-(p-toluene-sulfonylamide) diphenylamine, and 4,4'-bis($\alpha$,$\alpha$-dimethylbenzyl) diphenylamine. Blending such an antioxidant tends to allow the molded article to have heat resistance and also have contamination resistance (e.g., inhibition of discoloration).

Examples of the antioxidant that prevents ozone aging include N,N'-diphenyl-p-phenylenediamene (DPPD) and N-isopropyl-N'-phenyl-p-phenylenediamene (IPPD).

When the molded article of a chloroprene copolymer rubber according to the present embodiment is used as medical disposable gloves, appearances (in particular, color tone) and hygiene are considered important. Thus, as the antioxidant (E), a hindered phenolic antioxidant is preferably used. Examples of the hindered phenolic antioxidant include 2,2'-methylenebis-(4-ethyl-6-t-butylphenol) and 4,4'-methylenebis-(2,6-di-t-butylphenol).

The amount of the antioxidant (E) contained in the chloroprene copolymer latex composition according to the present embodiment is usually 0.1 to 10.0 parts by mass, preferably 0.5 to 5.5 parts by mass, more preferably 2.0 to 4.8 parts by mass, per 100 parts by mass of the solid content in the chloroprene copolymer latex (A). When the amount of the antioxidant (E) is within this range, a sufficient antioxidant effect is provided, the vulcanization treatment is not inhibited, and additionally, the color tone is unlikely to deteriorate.

To the chloroprene copolymer latex composition according to the present embodiment, other additives may be blended, if desired, in addition to the chloroprene copolymer latex (A), the metal oxide (B), the vulcanization accelerator (C), the sulfur (D), and the antioxidant (E), as long as the other additives are not contrary to the object of the present invention. Examples of the additives that can be blended include a pH adjuster, a filler, a pigment, a colorant, an antifoaming agent, and a thickener.

[Molded Article of Chloroprene Copolymer Rubber]

The chloroprene copolymer latex composition according to the present embodiment can be molded or cured to thereby provide a molded article. For example, the chloroprene copolymer latex composition according to the embodiment can be molded by a dip processing method to thereby provide a dip-molded product.

The chloroprene copolymer latex composition according to the present embodiment may be matured under predetermined conditions before the dip processing. The temperature conditions for the maturing is 15 to 40° C., and the maturing time is 15 to 72 hours. For example, conditions of maturing at 20° C. for 24 hours may be employed. The starting point of the maturing is the time point when the chloroprene copolymer latex (A) is mixed with all of the metal oxide (B), the vulcanization accelerator (C), the sulfur (D), and the antioxidant (E).

After the maturing, the steps of a dip and solidification treatment, drying, and vulcanization treatment (curing) are conducted in this order to thereby provide a molded article in a film form.

The dip and solidification treatment can be conducted by submerging a plate or mold coated with a coagulant in the chloroprene copolymer latex composition for a predetermined time to thereby deposit the solid content in the chloroprene copolymer latex composition, including the chloroprene copolymer, on the surface of the plate or mold. As the coagulant, a metal salt can be used. For example, a nitrate can be used.

In order to avoid the problem of the appearance of the molded article, such as generation of a blister or pinhole, a drying step at a relatively low temperature of 70° C. or more and 100° C. or less (roughly drying step) may be conducted before the vulcanization step.

The vulcanization temperature in the vulcanization step can be 100° C. in air, for example. The vulcanization time at this vulcanization temperature can be 20 minutes or more and 60 minutes or less, for example. Sufficient vulcanization treatment is preferably conducted to the extent that the tensile strength and tensile elongation ratio of the molded article do not deteriorate.

Vulcanizing the composition deposited on the surface of the plate or mold under the above conditions can provide a molded article of a chloroprene copolymer rubber. The molded article of a chloroprene copolymer rubber preferably has a 100% elastic modulus of 0.6 MPa or more and 0.65 MPa or less, a 500% elastic modulus of 0.5 MPa or more and 1.6 MPa or less, a tensile strength of 17 MPa or more and 35 MPa or less, and a tensile elongation ratio of 800% or more and 1500% or less. The 100% elastic modulus is used as an index for the flexibility. A smaller 100% elastic modulus value indicates higher flexibility. The chloroprene copolymer latex rubber molded article according to the present embodiment has excellent flexibility. The molded article also undergoes only a small change in the physical properties between before and after the thermal degradation treatment and has an excellent change over time.

[Medical Disposable Gloves]

The molded article of a chloroprene copolymer rubber can be suitably used particularly as medical disposable gloves.

The molded article of a chloroprene copolymer rubber has preferably a 100% elastic modulus of 0.65 MPa or less because flexibility is achieved in medical disposable gloves. Regarding the lower limit, the 100% elastic modulus of the molded article of a chloroprene copolymer rubber may be 0.6 MPa or more, for example.

When the molded article of a chloroprene copolymer rubber has a 500% elastic modulus of 0.5 MPa or more, the medical disposable gloves has a soft feeling of use and is less fatiguing even if used for a long period. The molded article of a chloroprene copolymer rubber preferably has a 500% elastic modulus of 1.6 MPa or less because the force to return is appropriate when fingers are bent in the medical disposable gloves.

The molded article of a chloroprene copolymer rubber preferably has a tensile strength of 17 MPa or more because breaks of the medical disposable gloves are unlikely to occur. Regarding the upper limit of the tensile strength of the molded article of a chloroprene copolymer rubber may be 35 MPa or less, for example.

The molded article of a chloroprene copolymer rubber preferably has a tensile elongation ratio of 800% or more because breaks of the medical disposable gloves are unlikely to occur. Regarding the upper limit, the tensile elongation ratio of the molded article of a chloroprene copolymer rubber may be 1500% or less, for example.

EXAMPLES

Hereinafter, the present invention will be further described in detail with reference to examples, but the present invention is not intended to be limited to these examples.

Example 1

(1) Preparation of Chloroprene Copolymer Latex (A)

To a reactor having an internal volume of 5 L, fed were 1200 g of 2-chloro-1,3-butadiene (A-1), 300 g of 2-methyl-1,3-butadiene (A-2), 1290 g of pure water, 65 g of disproportionated rosin acid (manufactured by Arakawa Chemical Industries, Ltd., R-600), 17.1 g of potassium hydroxide, 3.9 g of sodium hydroxide, 3.3 g of a sodium salt of a β-naphthalenesulfonic acid-formalin condensate, and 1.65 g of n-dodecylmercaptan. The starting materials fed in the reactor were emulsified, and the rosin acid was turned into rosin acid soap.

2-chloro-1,3-butadiene (A-1) and 2-methyl-1,3-butadiene (A-2) were blended as starting monomers, and pure water was blended as a dispersion medium for emulsion polymerization. Rosin acid, potassium hydroxide, and sodium hydroxide were blended as materials for an emulsifier, and the sodium salt of a β-naphthalenesulfonic acid-formalin condensate was blended as an emulsifier.

To an emulsion provided by emulsifying the starting materials, 4 g of potassium persulfate was added as a polymerization initiator, and emulsion polymerization was conducted under a nitrogen gas atmosphere at 30° C. When the polymerization conversion of all the monomers reached 84% by mass, the polymerization was terminated. Subsequently, unreacted 2-chloro-1,3-butadiene (A-1) and 2-methyl-1,3-butadiene (A-2) were removed by steam distillation to provide a chloroprene copolymer latex (A).

The polymerization conversion was calculated as follows. Specifically, the emulsion was collected after the start of the polymerization, and the collected emulsion was allowed to stand in an oven at 141° C. for 30 minutes for drying to thereby provide a dried solid substance. The dried solid substance provided included a polymer and solid content other than the polymer. Then, the mass of the component that did not evaporate at 141° C. among the various components used for the emulsion polymerization was calculated from the amount of the polymerization material fed, and was used as the mass of the solid content other than the polymer. A value obtained by subtracting the mass of the solid content other than the polymer from the mass of the dried solid substance provided by drying the emulsion after the start of the polymerization was used as the "amount of the chloroprene copolymer produced," and the polymerization conversion was calculated by the expression (1). The polymerization conversion calculated is shown in Table 1.

Polymerization conversion [% by mass]=[(amount of chloroprene copolymer produced)/(total mass of total monomers fed)]×100     (1)

The "mass of the total monomers fed" in the expression (1) is the amount of all the monomers fed that was included in the emulsion collected to provide the dried solid substance.

Additionally, the various physical properties of the chloroprene copolymer latex (A) provided were evaluated.

(i) The Tetrahydrofuran Insoluble Content in Chloroprene Copolymer:

The tetrahydrofuran insoluble content of the chloroprene copolymer was measured as follows. Specifically, at 25° C., 1 g of chloroprene copolymer latex (A) was added dropwise to 100 mL of tetrahydrofuran and shaken on a shaker (SA300) manufactured by Yamato Scientific Co., Ltd. for 10 hours. The mixture of the chloroprene copolymer latex (A) and tetrahydrofuran after the shaking treatment was subjected to separation by centrifugal sedimentation using a centrifugal sedimentation separator (manufactured by KOKUSAN Co. Ltd., H-9R) to provide a dissolution phase as a supernatant. The dissolution phase provided was heated to 100° C. to evaporate the tetrahydrofuran over an hour, and the mass of the dried solid substance was measured. This provides the mass of the dissolved matters that were dissolved in the dissolution phase out of the chloroprene copolymer.

The mass of the chloroprene copolymer in 1 g of the chloroprene copolymer latex (A) and the mass of the above dissolved matters were substituted into the expression (2) to calculate the tetrahydrofuran insoluble content that did not dissolve in tetrahydrofuran at 25° C. out of the chloroprene copolymer. The tetrahydrofuran insoluble content measured is shown in Table 1.

The tetrahydrofuran insoluble content (% by mass)
={1−[(mass of dissolved matters)/(mass of chloroprene copolymer in 1 g of chloroprene copolymer latex(A))]}×100     (2)

The mass of the chloroprene copolymer in 1 g of the chloroprene copolymer latex (A) in the expression (2) was considered as the mass of the solid content provided by drying 1 g of the chloroprene copolymer latex (A) to solid. Here, the chloroprene copolymer latex (A) was allowed to stand in an oven at 141° C. for 30 minutes for drying to solid.

(ii) Weight Average Molecular Weight (Mw):

An exemplary method for determining the weight average molecular weight (Mw) of tetrahydrofuran soluble component at 25° C. in the chloroprene copolymer will be described below. In the same processing as for the sample preparation for the measurement of tetrahydrofuran insoluble content described above, a dissolution phase as a supernatant after separation by centrifugal sedimentation was prepared, separated, and diluted with tetrahydrofuran to prepare a sample. The sample provided was subjected to molecular weight measurement in terms of polystyrene by GPC (gel permeation chromatography method) to measure the weight average molecular weight (Mw).

As for the GPC measurement conditions, LC-20AD manufactured by Shimadzu Corporation as a GPC measurement apparatus and RID-10A (refractive index detector) manufactured by Shimadzu Corporation as a detector were used. The type of column used was PLgel 10 μm Mini-MIX-B manufactured by Agilent Technologies, Inc., the eluant was tetrahydrofuran (KANTO CHEMICAL CO., INC., for HPLC), the column temperature was 40° C., and the flow rate was 0.4 ml/min.

(iii) Monomer Unit Content in Chloroprene Copolymer:

The content of the component derived from 2-methyl-1,3-butadiene (A-2) in the chloroprene copolymer was determined by $^1$H-NMR analysis. The chloroprene copolymer latex provided was coagulated with methanol. After drying, deuterated chloroform was added to the coagulated product provided. The substance insoluble in deuterated chloroform was filtered off, and the solution provided was subjected to $^1$H-NMR analysis. For the $^1$H-NMR analysis, JNM-AL400 manufactured by JEOL Ltd was used as the measurement apparatus, and tetramethylsilane was used as a reference for the chemical shift.

The content of the component derived from 2-methyl-1,3-butadiene (A-2) was calculated from the peak area of a peak (5.4 ppm) assigned to 2-chloro-1,3-butadiene (A-1) and a peak (5.1 ppm) assigned to 2-methyl-1,3-butadiene (A-2) in the $^1$H-NMR spectrum by the expression (3).

Content of component derived from 2-methyl-1,3-butadiene (A-2) (%)=(area of peak at 5.1 ppm)/(area of peak at 5.1 ppm+area of peak at 5.4 ppm)×100     (3)

When the monomer (A-3) is contained but exhibits no peak overlapping the peak at 5.1 ppm or the peak at 5.4 ppm, the expression (3) can be used for determining the proportion of 2-methyl-1,3-butadiene (A-2) with respect to the total of 2-chloro-1,3-butadiene (A-1) and 2-methyl-1,3-butadiene (A-2). When the proportion of the monomer (A-3) contained is determined, the proportion of the monomer (A-3) with respect to the total of the 2-chloro-1,3-butadiene (A-1) and the monomer (A-3) is calculated by an expression similar to the expression (3), by use of the peak area of peaks overlapping neither the peaks of 2-chloro-1,3-butadiene (A-1) nor 2-methyl-1,3-butadiene (A-2) among peaks assigned to the monomer (A-3). Similarly, the proportion of the monomer (A-3) in the total monomer components constituting the chloroprene polymer is also determined.

When the monomer (A-3) exhibits peaks overlapping the peak at 5.1 ppm and the peak at 5.4 ppm, the respective peaks assigned to 2-chloro-1,3-butadiene (A-1), 2-methyl-1,3-butadiene (A-2), and the monomer (A-3) are identified using multidimensional NMR measurement results such as $^1$H-$^1$H COSY (COrrelation SpectroscopY), and the peak area can be used for the similar calculation to thereby determine the proportion of each substance.

(2) Preparation of Chloroprene Copolymer Latex Composition 100 parts by mass of the chloroprene copolymer latex (A) provided in the above (1), 3.7 parts by mass of zinc oxide (AZ-SW manufactured by Osaki Industry Co., Ltd.), 1.0 part by mass of zinc dibutyldithiocarbamate (NOCCELER (registered trademark) BZ manufactured by Ouchi Shinko Chemical Industrial Co., Ltd.), 1.0 part by mass of zinc 2-mercaptobenzothiazole (NOCCELER (registered trademark) MZ manufactured by Ouchi Shinko Chemical Industrial Co., Ltd.), and 0.5 parts by mass of diphenyl guanidine (NOCCELER (registered trademark) D manufactured by Ouchi Shinko Chemical Industrial Co., Ltd.) as vulcanization accelerators, 0.45 parts by mass of sulfur (5-50 manufactured by Nippon Color Ind. Co., Ltd.), and 2.0 parts by mass of a phenolic antioxidant (K-840 manufactured by Chukyo Yushi Co., Ltd.) were fed in a vessel equipped with a stirrer. These components were stirred for 20 minutes and homogeneously mixed to provide a chloroprene copolymer latex composition. The chloroprene copolymer latex composition after stirring was allowed to stand at 20° C. for 24 hours for maturing.

The zinc oxide AZ-SW, sulfur S-50, and phenolic antioxidant K-840 were each in the form of a dispersion, which includes the zinc oxide (B), the sulfur (D), or the antioxidant (E) as an active ingredient dispersed in a liquid medium. The amount of each of the above-described zinc oxide AZ-SW, sulfur S-50, and phenolic antioxidant K-840 fed is only the amount of the active ingredient of each of the zinc oxide AZ-SW, the sulfur S-50, and the K-840 fed.

(3) Production of Film

The chloroprene copolymer latex composition provided in the above (2) was used to mold a film of the chloroprene copolymer by the dip processing method.

As a mold for a film of the chloroprene copolymer, a ceramic plate of 200 mm in length, 100 mm in width, and 5 mm in thickness was provided. This mold was dipped in a 30% by mass calcium nitrate aqueous solution, then withdrawn, and dried in an oven at 40° C. for 10 minutes to thereby cause calcium nitrate, as a coagulant, to adhere to the surface of the mold.

Further, the dried mold was dipped in the chloroprene copolymer latex composition provided in the above (2) to cause the solid content of the chloroprene copolymer latex composition to deposit on the surface of the mold. The mold was withdrawn from the chloroprene copolymer latex composition and then dried in an oven at 70° C. for 30 minutes.

Next, the mold with the solid content deposited on the surface thereof was heated in an oven at 100° C. for 20 minutes to cure the solid content of the chloroprene copolymer latex composition deposited on the surface of the mold by vulcanization treatment. After left to cool under atmospheric air, the molded article cured on the surface of the mold was cut into a desired shape and size to thereby provide a film as a molded article of the vulcanized chloroprene copolymer rubber.

The film was cut so as to correspond to the No. 6 dumbbell specified in JIS K6251-2017 to provide a specimen. The specimen has a thickness of 0.15 to 0.25 mm. Then, this specimen was heat-treated in air at 100° C. for 22 hours for thermal degradation treatment. Both before and after the thermal degradation treatment, the specimen was subjected to a tensile test at 23° C. by a method in accordance with JIS K6251-2017, and thus, the tensile strength, the tensile elongation ratio, the elastic modulus at 100% elongation (100% elastic modulus), and the elastic modulus at 500% elongation (500% elastic modulus) were measured. The various physical properties of the film measured as described above are summarized in Table 1. In Table 1, "Weight average molecular weight (Mw)" in the rows of the Latex physical properties is the weight average molecular weight of the tetrahydrofuran soluble component at 25° C. in the chloroprene copolymer.

Example 2

A copolymer latex composition, a film, and a specimen were produced in the same manner as in Example 1 except that the amount of each of 2-chloro-1,3-butadiene and 2-methyl-1,3-butadiene fed was changed as shown in Table 1 and that the polymerization conversion at the completion of the reaction was set to 76% by mass to prepare the chloroprene copolymer latex (A). Various evaluations were conducted in the same manner as in Example 1. The results are shown in Table 1.

Example 3

A copolymer latex composition, a film, and a specimen were produced in the same manner as in Example 1 except that the polymerization conversion at the completion of the reaction was set to 64% by mass to prepare the chloroprene copolymer latex (A). Various evaluations were conducted in the same manner as in Example. The results are shown in Table 1.

Example 4

A copolymer latex composition, a film, and a specimen were produced in the same manner as in Example 1 except that the amount of each of 2-chloro-1,3-butadiene, 2-methyl-1,3-butadiene, and 2,3-dichloro-1,3-butadiene fed was changed as shown in Table 1 and that the polymerization conversion at the completion of the reaction was set to 83% by mass to prepare the chloroprene copolymer latex (A). Various evaluations were conducted in the same manner as in Example 1. The results are shown in Table 1.

Comparative Example 1

A copolymer latex composition, a film, and a specimen were produced in the same manner as in Example 1 except that the amount of each of 2-chloro-1,3-butadiene, 2-methyl-1,3-butadiene, and n-dodecylmercaptan fed was changed as shown in Table 1 and that the polymerization conversion at the completion of the reaction was set to 90% by mass to prepare the chloroprene copolymer latex (A). Various evaluations were conducted in the same manner as in Example 1. The results are shown in Table 1.

Comparative Example 2

A copolymer latex composition, a film, and a specimen were produced in the same manner as in Example 1 except that the amount of each of 2-chloro-1,3-butadiene and 2-methyl-1,3-butadiene fed was changed as shown in Table 1 and that the polymerization conversion at the completion of the reaction was set to 82% by mass to prepare the chloroprene copolymer latex (A). Various evaluations were conducted in the same manner as in Example 1. The results are shown in Table 1.

Comparative Example 3

A copolymer latex composition, a film, and a specimen were produced in the same manner as in Example 1 except that the amount of each of 2-chloro-1,3-butadiene and 2-methyl-1,3-butadiene fed was changed as shown in Table 1 and that the polymerization conversion at the completion of the reaction was set to 60% by mass to prepare the chloroprene copolymer latex (A). Various evaluations were conducted in the same manner as in Example 1. The results are shown in Table 1.

Comparative Example 5

A copolymer latex composition, a film, and a specimen were produced in the same manner as in Example 1 except that the amount of n-dodecylmercaptan fed was changed as shown in Table 1 and that the polymerization conversion at the completion of the reaction was set to 82% by mass to prepare the chloroprene copolymer latex (A). Various evaluations were conducted in the same manner as in Example 1. The results are shown in Table 1.

TABLE 1

|  |  | Example | | | | Comparative Example | | | | |
| --- | --- | --- | --- | --- | --- | --- | --- | --- | --- | --- |
|  |  | 1 | 2 | 3 | 4 | 1 | 2 | 3 | 4 | 5 |
| Polymerization conditions | Amount of 2-chloro-1,3-butadiene (A-1) used (parts by mass) [(mol %)] | 80 [75.5] | 71 [65.3] | 80 [75.5] | 77 [73.2] | 100 [100] | 90 [87.4] | 56 [49.5] | 80 [75.5] | 80 [75.5] |
|  | Amount of 2-methyl-1,3-butadiene (A-2) used (parts by mass) [(mol %)] | 20 [24.5] | 29 [34.7] | 20 [24.5] | 20 [24.7] | 0 [0] | 10 [12.6] | 44 [50.5] | 20 [24.5] | 20 [24.5] |
|  | Amount of 2,3-dichloro-1,3-butadiene (A-3) used (parts by mass) [(mol %)] | 0 | 0 | 0 | 3 [2.1] | 0 | 0 | 0 | 0 | 0 |
|  | Amount of n-dodecylmercaptan used (parts by mass) | 0.11 | 0.11 | 0.11 | 0.11 | 0.16 | 0.11 | 0.11 | 0.11 | 0.011 |
|  | Polymerization conversion (% by mass) | 84 | 76 | 64 | 83 | 90 | 82 | 67 | 60 | 82 |
| Physical properties of latex | Solid content (% by mass) | 45 | 42 | 37 | 45 | 48 | 46 | 36 | 33 | 44 |
|  | Tetrahydrofuran insoluble content (% by mass) | 2 | 0 | 0 | 4 | 0 | 0 | 0 | 0 | 33 |
|  | Weight average molecular weight (Mw) ($\times 10^6$) | 5.9 | 7.7 | 9.9 | 5.9 | 7.3 | 4.0 | 7.9 | 5.1 | 7.4 |
|  | Proportion of monomer units derived from 2-methyl-1,3-butadiene in copolymer (mol %) | 14% | 20% | 11% | 13% | 0 | 6% | 28% | 9% | 13% |
| Mechanical properties of chloroprene copolymer rubber | Before thermal degradation treatment | | | | | | | | | |
|  | 100% elastic modulus (MPa) | 0.63 | 0.49 | 0.55 | 0.60 | — | 0.44 | 0.54 | 0.40 | 0.70 |
|  | 500% elastic modulus (MPa) | 1.28 | 0.89 | 1.05 | 1.04 | — | 0.74 | 0.93 | 0.82 | 1.83 |
|  | Tensile strength (MPa) | 18.9 | 17.1 | 18.4 | 18.8 | — | 16.1 | 14.6 | 15.8 | 15.1 |
|  | Tensile elongation ratio (%) | 1150 | 1200 | 1150 | 1250 | — | 1275 | 1200 | 1200 | 1030 |
|  | After thermal degradation treatment | | | | | | | | | |
|  | 100% elastic modulus (MPa) | 0.59 | 0.53 | 0.54 | 0.62 | — | 0.54 | 0.39 | 0.44 | 0.53 |
|  | 500% elastic modulus (MPa) | 1.34 | 1.14 | 1.14 | 1.28 | — | 1.08 | 0.97 | 1.01 | 1.39 |
|  | Tensile strength (MPa) | 19.2 | 18.0 | 17.0 | 19.4 | — | 20.9 | 11.7 | 16.1 | 16.5 |
|  | Tensile elongation ratio (%) | 1050 | 1000 | 1050 | 1075 | — | 1075 | 1000 | 1050 | 960 |
|  | Change between before and after thermal degradation treatment | | | | | | | | | |
|  | Change in 100% elastic modulus (%) | 107 | 92 | 102 | 97 | — | 81 | 138 | 91 | 132 |
|  | Change in 500% elastic modulus (%) | 96 | 78 | 92 | 81 | — | 69 | 96 | 81 | 132 |
|  | Change in tensile strength (%) | 98 | 95 | 108 | 97 | — | 77 | 125 | 98 | 92 |
|  | Change in tensile elongation ratio (%) | 110 | 120 | 110 | 116 | — | 119 | 120 | 114 | 107 |

2-methyl-1,3-butadiene fed was changed as shown in Table 1 and that the polymerization conversion at the completion of the reaction was set to 67% by mass to prepare the chloroprene copolymer latex (A). Various evaluations were conducted in the same manner as in Example 1. The results are shown in Table 1.

Comparative Example 4

A copolymer latex composition, a film, and a specimen were produced in the same manner as in Example 1 except In Examples 1 to 4, in which the chloroprene copolymer in the latex contains the monomer units derived from 2-methyl-1,3-butadiene, more crosslinked structures were formed by the vulcanization treatment at 100° C. in comparison with Comparative Example 1, in which the polymer in the latex contains no monomer units derived from 2-methyl-1,3-butadiene, thereby Examples 1 to 4 provide films having high flexibility and strength. In Comparative Example 1, it was impossible to remove the film from the mold after the vulcanization treatment, and the evaluation was not be conducted. The tensile strengths (before thermal degradation treatment) of the molded articles provided in Comparative Examples 2 to 5 are insufficient for surgical gloves.

A comparison between Examples 1 to 4 and Comparative Examples 2 to 4 shows the following: the strength is little when the proportion of the monomer units derived from 2-methyl-1,3-butadiene included in the chloroprene copolymer in the latex is 10 mol % or less; the strength increases as the proportion thereof increases; and, however, the strength decreases when the proportion exceeds 27 mol %.

In Comparative Example 5, the tetrahydrofuran insoluble content is high. Thus, the flexibility decreases, and the elongation ratio and tensile strength of the film decrease.

The invention claimed is:

1. A latex of a chloroprene copolymer consisting of monomer units derived from 2-chloro-1,3-butadiene (chloroprene) and monomer units derived from 2-methyl-1,3-butadiene, wherein
    a tetrahydrofuran insoluble content in the chloroprene copolymer is 20% by mass or less,
    a weight average molecular weight of a tetrahydrofuran soluble component at 25° ° C. of the chloroprene copolymer is 550,000 or more, and
    a proportion of the monomer units derived from 2-methyl-1,3-butadiene in the chloroprene copolymer is 10 to 27 mol %.

2. A method for producing a chloroprene copolymer latex according to claim 1, comprising a step of emulsion-copolymerizing monomer components containing 2-chloro-1,3-butadiene (chloroprene) and 2-methyl-1,3-butadiene, wherein
    a proportion of 2-methyl-1,3-butadiene in the total monomer components is 2 to 40 mol %, and a polymerization conversion of the total monomers is 61 to 90% by mass.

3. The method for producing a chloroprene copolymer latex according to claim 2, wherein an alkylmercaptan is used as a chain transfer agent.

4. The method for producing a chloroprene copolymer latex according to claim 2, wherein a potassium salt of rosin acid is used as an emulsifier.

5. A chloroprene copolymer latex composition comprising:
    100 parts by mass of solid content of a chloroprene copolymer latex;
    0.1 to 20.0 parts by mass of a metal oxide (B);
    0.1 to 10.0 parts by mass of a vulcanization accelerator (C);
    0.1 to 10.0 parts by mass of sulfur (D); and
    0.1 to 10.0 parts by mass of an antioxidant (E),
    wherein a chloroprene copolymer included in the chloroprene copolymer latex consists of monomer units derived from 2-chloro-1,3-butadiene (chloroprene) and monomer units derived from 2-methyl-1,3-butadiene,
    a tetrahydrofuran insoluble content in the chloroprene copolymer is 20% by mass or less, and
    a proportion of the monomer units derived from 2-methyl-1,3-butadiene in the chloroprene copolymer is 10 to 27 mol %.

6. A molded article of a chloroprene copolymer rubber, provided by curing the chloroprene copolymer latex composition according to claim 5.

7. A dip-molded product provided by molding the chloroprene copolymer latex composition according to claim 5 by a dipping method followed by curing.

8. The dip-molded product according to claim 7, wherein the dip-molded product is gloves.

9. The dip-molded product according to claim 8, wherein the dip-molded product is medical disposable gloves.

* * * * *